United States Patent [19]

Iderosa

[11] Patent Number: 5,065,515
[45] Date of Patent: Nov. 19, 1991

[54] THERMALLY ASSISTED SHAVING SYSTEM

[75] Inventor: Richard A. Iderosa, West Haven, Conn.

[73] Assignee: Warner-Lambert Company, Morris Plains, N.J.

[21] Appl. No.: 647,162

[22] Filed: Jan. 24, 1991

[51] Int. Cl.⁵ .......................... A61B 17/00; B26B 1/00
[52] U.S. Cl. ............................................. 30/140; 83/16; 132/200; 606/9; 606/28
[58] Field of Search ................ 30/140, 123; 83/171, 83/16; 219/222, 229; 606/28, 9, 13; 132/200

[56] References Cited

U.S. PATENT DOCUMENTS

| | | | |
|---|---|---|---|
| 2,298,508 | 10/1942 | Peters | 30/140 X |
| 2,324,148 | 7/1943 | Gravin | 30/140 X |
| 4,209,017 | 6/1980 | Shaw | 30/140 X |
| 4,231,371 | 11/1980 | Lipp | 30/140 X |
| 4,819,669 | 4/1989 | Politzer | 606/9 X |

Primary Examiner—Douglas D. Watts
Attorney, Agent, or Firm—Daniel A. Scola, Jr.; Richard S. Bullitt

[57] ABSTRACT

A device for shaving hair has a housing which is formed with a handle and which supports a razor blade and a heating means. More specifically, the heating means, which may be either a linearly-scanned laser beam or a ceramic or metallic heating element, is mounted in the housing to pre-heat the hair to be cut. Accordingly, the heating means softens the hair that is near the cutting edge of the blade, so that a blade which is less sharp than conventional blades may be used to cut the hair without unduly irritating the skin. Appropriate power supplies for the heating means may be contained within the housing, if desired.

17 Claims, 2 Drawing Sheets

THERMALLY ASSISTED SHAVING SYSTEM

FIELD OF THE INVENTION

The present invention relates generally to devices which cut hair. More particularly, the present invention relates to shaving devices which shave the hair on the surface of skin. The present invention is particularly, though not exclusively, useful for shaving hair on a surface of skin without requiring wetting or pre-lubrication of the skin.

BACKGROUND OF THE INVENTION

Many devices exist for removing hair from a skin surface. Among the most common of these devices is the safety razor which cuts hair by means of a very sharp razor blade. Unfortunately, sharp blades can produce undesirable results, such as nicking and cutting of the skin. Therefore, in order to reduce nicking and irritation, a lubricating solution, such as soap and water or shaving cream, must typically be applied to the skin prior to shaving. This can be inconvenient and, unfortunately, does not completely eliminate nicking or other forms of skin irritation. On the other hand, a dull blade, though perhaps less likely to nick or irritate skin, cannot cut hair, under ordinary circumstances, as efficaciously as a sharper blade.

To avoid skin irritation problems and the inconveniences noted above that are associated with so-called "wet" shaving, a number of devices have been introduced which remove hair without the use of a razor blade. For example, hair depilation devices have been proposed which remove hair by heating or by irradiating the hair follicles. The principle of these devices is that as hair is heated, it becomes softer and easier to remove from the skin. Unfortunately, in order to remove hair solely by heating the hair, a relatively large amount of heat must be directed onto the hair. These relatively large amounts of heat must be precisely controlled to avoid injuring the skin. The requirement for precise control of the heat results in hair depilation devices which are relatively expensive and which typically require an expert operator. Accordingly, inexpensive, simple, easy to use devices such as safety razors are still preferred. The present invention recognizes that a relatively dull razor blade which is less likely to nick or cut the skin than a relatively sharp blade can be used to shave hair by exposing the hair to a relatively small amount of heat to soften the hair immediately before the hair is cut by the blade.

It is therefore an object of the present invention to provide a shaving system which uses a razor blade to cut hair, but which does not require prelubrication of the skin. It is a further object of the present invention to provide a shaving system which cuts hair without requiring prelubrication of the skin and without requiring an expert operator. Another object of the present invention is to provide a shaving system which is easy to use and comparatively cost-effective to manufacture.

SUMMARY

A device for shaving hair includes a housing which is formed with a handle and which supports a cutting blade and a means for heating the hair to be cut. The heating means is a source of electromagnetic radiation, preferably a laser, or a source of infrared radiation, such as a metallic heating element. More specifically, in the preferred embodiment a laser generating apparatus may be mounted in the housing to scan and focus a laser beam onto the hair near the cutting edge of the blade.

The laser generating apparatus itself has a source of laser light. The laser beam produced by the source is passed through optical collimating components and subsequently directed onto a scanning mirror. The scanning mirror is oscillated by a galvanometric scanner to linearly scan the laser beam onto a lens. As the beam is scanned onto the lens in a line across one face of the lens, the angles of incidence of the beam relative to the lens vary along the line of incidence. In accordance with the present invention, the lens is configured to refract the beam, which is incident on the lens at various angles along the length of the line, such that the beam exits the lens in parallel paths. Next, the beam is passed through a focussing blade, which focusses the beam in a line a few microns distant from the blade. This line is near the cutting edge of the razor blade and is substantially parallel to the cutting edge of the blade.

Alternatively, the laser apparatus may be dispensed with and another source of radiated heat, such as a nickel-chromium element which is electrically heated, may be mounted in the housing near the cutting edge of the blade. The heating element may be formed with a bevelled edge through which heat will preferentially be dissipated. The heating element is positioned in the housing so that its bevelled edge is close to and parallel with the cutting edge of the razor blade. Importantly, hair which is heated by the laser or heating element is thereby softened and made easier to cut. Thus, a blade that is less sharp than conventional razor blades may be used.

To energize the laser apparatus or heating element, as appropriate, a battery may be contained in the housing. On the other hand, appropriate electronic componentry may be included in the housing to transform power from an electrical outlet into an energy form which is useful for energizing the laser or heating element.

The novel features of this invention, as well as the invention itself, both as to its structure and its operation, will be best understood from the accompanying drawings, taken in conjunction with the accompanying description, in which similar reference characters refer to similar parts, and in which:

DESCRIPTION OF THE PREFERRED EMBODIMENT

Figure 1:
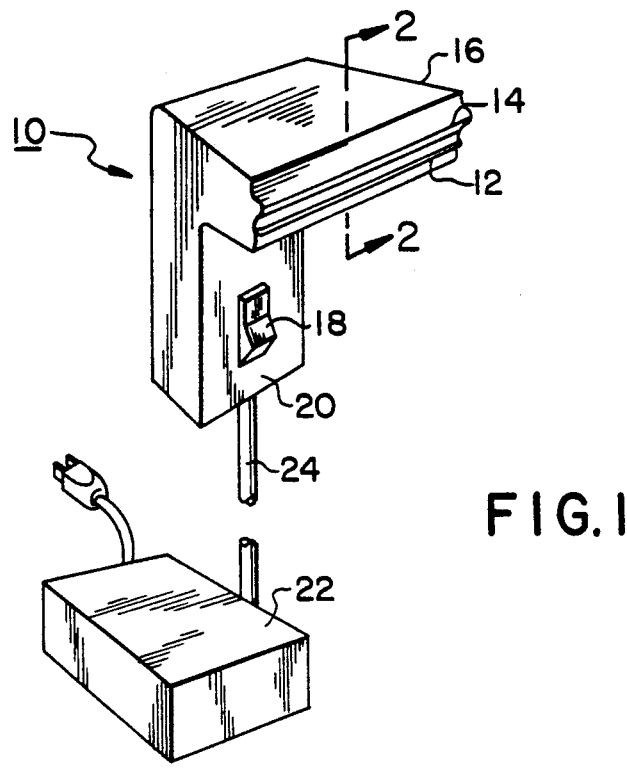
FIG. 1 is an isometric view of the novel thermally assisted shaving device.

Referring initially to FIG. 1, a thermally assisted shaving device is shown and generally designated 10. As shown, device 10 includes a cutting blade 12 and a laser focussing blade 14, both of which are fixedly held in an electrically resistive ceramic housing 16. A switch 18 is also shown operatively mounted in a handle 20 of the housing 16 for selectively energizing and deenergizing device 10. FIG. 1 further shows that device 10 may be energized by a power supply 22, which may be either a direct current (dc) or alternating current (ac) source of power. Power supply 22 is connected to device 10 through electrical cord 24. While FIG. 1 shows that device 10 is energized by an external power supply 22, it is to be understood that the present invention also envisions use of a dc power supply, such as a battery (not shown), which may be contained within the housing 16 to energize device 10.

Figure 2:
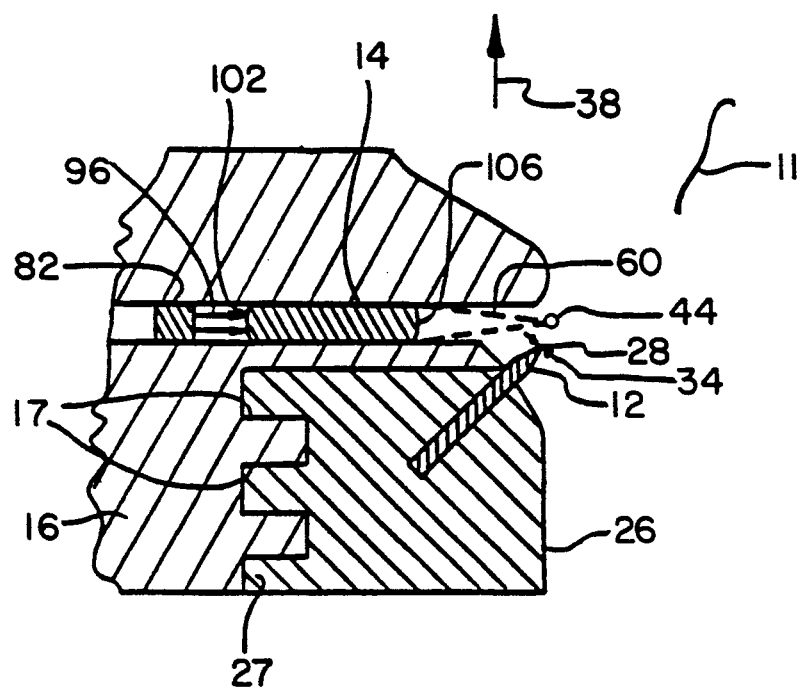
FIG. 2 is a cross-sectional view of the preferred embodiment of the novel thermally assisted shaving device as seen along the line 2—2 in FIG. 1.

The details of device 10 are best seen in reference to FIG. 2. There, housing 16 is shown to include a detachable ceramic blade cartridge 26, which fixedly holds blade 12. Blade cartridge 26, like housing 16, may alternatively be made of rubber or plastic. As shown, cartridge 26 has tongues 27 extending therefrom for engagement with grooves 17 of housing 16. It is to be appreciated that tongues 27 are engageable with grooves 17 in an interference fit. Accordingly, blade 12 may be replaced by replacing cartridge 26 with a new cartridge which also contains an appropriate razor blade. If desired, however, housing 16 could be a single integrated unit in which blade 12 is permanently mounted or, alternatively, is individually replaceable.

Still referring to FIG. 2, blade 12 is mounted in cartridge 26 by any suitable means, such as by solvent bonding blade 12 to cartridge 26. As shown, blade 12 defines a cutting edge 28, which protrudes from cartridge 26 for the purpose of cutting hair 11. Because the hairs to be cut by blade 12 are to be softened by preheating, as disclosed below, cutting edge 28 of blade 12 can be relatively less sharp than the cutting edges of conventional blades. Specifically, in the embodiment shown in FIG. 2, width 34 of cutting edge 28 is approximately on the order of a hundred microns.

Finally, FIG. 2 shows that housing 16 also contains the focussing blade 14 of a laser apparatus which will shortly be disclosed. Blade 14 may be held in housing 16 by any suitable means, such as by solvent bonding blade 14 to housing 16 or by attaching blade 14 to housing 16 with screws (not shown). The device shown in FIG. 2 focusses a linearly scanned laser beam, represented by dashed lines 60, onto a heating line which in its end view is represented by the dot 44 in FIG. 2. Laser beam 60 heats hair 11 prior to shaving the hair 11 with blade 12. To this end, heating line 44 is substantially co-planar with cutting edge 28 of blade 12, and is preferably but a few millimeters distant from cutting edge 28 to minimize heat loss from hairs which have been heated by beam 60 prior to the hairs being cut by blade 12.

Figure 3:
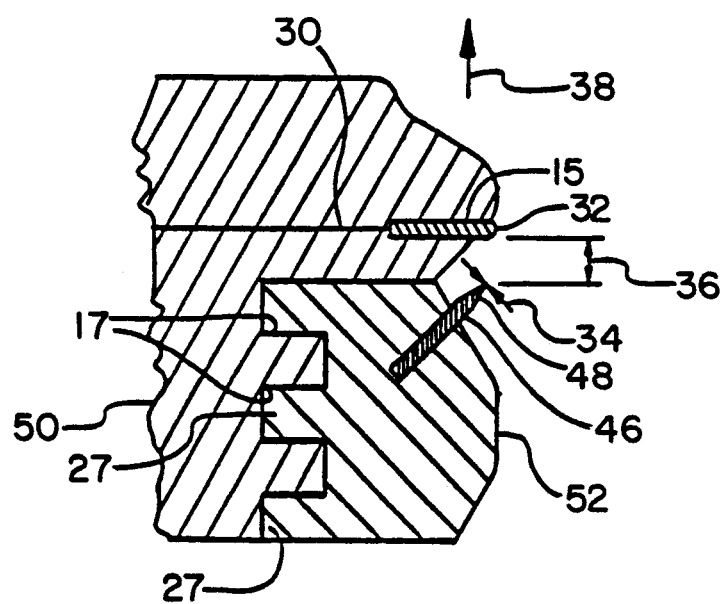
FIG. 3 is a cross-sectional view of an alternate embodiment of the novel thermally assisted shaving device as would be seen along the line 2—2 in FIG. 1.

In the alternate embodiment of device 10 shown in FIG. 3, focussing blade 14 has been replaced by a heating element 15. Element 15 is made of an electrically resistive material, which grows hotter when electricity is passed through it. In the preferred embodiment, element 15 is made of a nickel-chromium (NiCr) alloy. Importantly, heating element 15 may be heated through wire 30, which is connectable to the power supply 22 shown in FIG. 1 to heat the hairs and stratum corneum of the skin to be shaved. As also shown in FIG. 3, heating edge 32 of element 15 protrudes from a housing 50. A razor blade 46 which has a cutting edge 48 also protrudes from housing 50. Blade 46 is in all essential respects identical to the blade 12 shown in FIG. 2. Blade 46 may be integrally attached to housing 50 or removably mounted in housing 50, or be part of a replaceable cartridge 52 that is attachable to housing 50.

Importantly, in order to increase the radiated heat from element 15 near cutting edge 48, heating edge 32 may be bevelled or rounded, as shown in FIG. 3. As is well-known, heat is preferentially dissipated through such a bevelled, or thinner, portion of element 15 because such a portion is relatively electrically more resistive than other thicker portions of element 15 and will accordingly dissipate relatively more heat than the relatively thicker portions. Moreover, the distance 36 between cutting edge 48 and heating edge 32 is preferably relatively small. For purposes of the present invention distance 36 is on the order of a few millimeters. This is to ensure that as device 10 passes over a surface of skin (not shown) in the direction of arrow 38, the heating effect of blade 46 is optimized. Specifically, the closer heating edge 32 is to cutting edge 48, the less heat will be lost from hairs that are heated by heating element 15 before the hairs are cut by blade 46.

Figure 4:
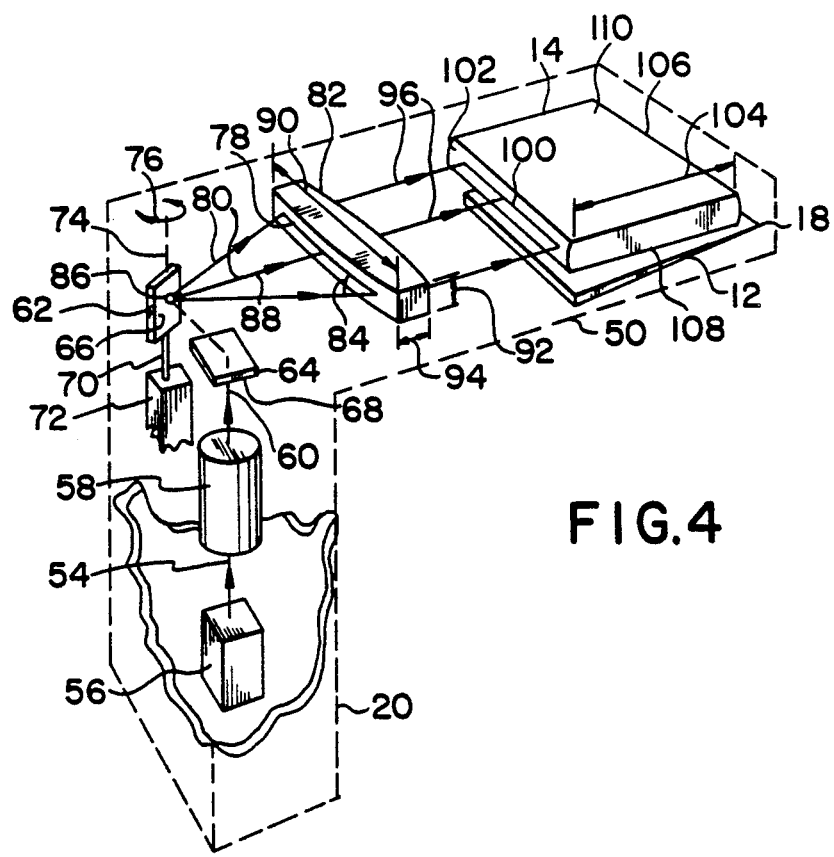
FIG. 4 is a schematic view showing the operable laser components of the preferred embodiment of the shaving device with the housing of the device shown in phantom for clarity.

The details of the heating laser of the device shown in FIG. 2 can be best appreciated in reference to FIGS. 2 and 4. It is to be understood that the following disclosure is merely exemplary of one laser apparatus which may be used with device 10. Other types of laser apparatus which can produce a linearly scanned laser beam and which are suitable for use with device 10 may also be used.

Cross-referencing FIGS. 2 and 4, it is to be understood that a laser beam, represented by arrow 54 in FIG. 4, is emitted by any suitable laser beam source 56. Laser beam source 56 may be any one of a number of laser beam sources including a YAG laser, a carbon dioxide ($CO_2$) laser, or a diode laser which emits a laser beam having an approximate wavelength of 840 nanometers (nm). A diode laser which emits a beam of approximately 840 nm is preferred because such a beam is more readily absorbed by hair than by skin. Importantly, to facilitate dexterous use of device 10, it is preferable that source 56 be relatively small and light weight.

In any case, laser beam 54 is optically coupled to collimator 58 by fiber optic lines (not shown) or by line-of sight. Collimator 58 is any suitable device which transmissively or reflectively collimates laser beam 54. The shape and size of the beam 60 as it exits collimator 58 will vary according to the particular source 56 and collimator 58 being used. For example, if collimator 58 transforms incident laser beam 54 into a coherent pencil beam, beam 60 will have an approximate diameter of between two and three millimeters. It will be understood that independent of the type of collimator 58 or laser source 56 being used, collimator 58 may be an integral component of laser source 56. In addition, collimator 58 and laser source 56, whether they are separated or joined as a single integral unit, may be housed in either power supply 22 or housing 50, as desired.

After being collimated by collimator 58, the laser beam 60 is directed against a scanning mirror 62. In the embodiment shown in FIG. 4, laser beam 60 is first reflected by a folding mirror 64 onto the scanning mirror 62. For the embodiment shown in FIG. 4, the mirrors 62 and 64 are preferably both low mass, thin reflectors of the standard quarter-wave or half-wave variety. In addition, the reflecting surfaces 66 and 68 of mirrors 62 and 64, respectively, are coated with a reasonably high reflectivity coating, the thickness of which depends on the particular wavelength of laser light being used. As is well known in the art, such coating increases the light reflectivity coefficient of laser beam reflectors and lenses. As is also well known, such a coating may have one or more layers of coating material.

As further shown in FIG. 4, scanning mirror 62 is fixedly attached to a shaft 70, which is in turn rotatably mounted for oscillating motion on a scanner 72 for purposes more fully disclosed below. Scanner 72 may be any suitable device for oscillating shaft 70 (and, hence, scanning mirror 62) at an appropriate frequency and through an appropriate scanning angle. In particular, the embodiment shown in FIG. 4 contemplates the use of a suitable commercially available galvanometric scanner 72. Depending on the potential needs for the operation of device 10, scanner 72 may be of the resonant type (i.e., single oscillation frequency), for simpler electronic componentry requirements, or may be a servo controlled galvanometric scanner. Such a servo controlled scanner provides a capability to vary scanner 72 oscillation as appropriate for particular device 10 stroke speeds across the surface to be shaved. In either case, the method of coupling scanning mirror 62 with scanner 72 should substantially prevent translational motion of scanning mirror 62 relative to scanner 72. Such translational displacement between scanning mirror 62 and scanner 72 will result in a failure to achieve a parallel scan, as well as increase beam aberrations at the skin surface.

As contemplated by the present invention, scanner 72 provides for substantially rotational-only motion between scanner 72 and scanning mirror 62. Scanner 72 does this by oscillating scanning mirror 62 about an axis 74 of the shaft 70 in the directions indicated by arrow 76. As seen in FIG. 4, scanning mirror 62, when appropriately oscillated by scanner 72, causes the laser beam 60 to move back and forth through orientations that are variously indicated by the lines 80. This causes beam 60 to impinge on a scan lens 82 in a line 78.

It will be appreciated in reference to FIG. 4 that the scanned beam 60, as represented by the lines 80, impinges on lens 82 at various angles of incidence 84 along the line 78. Moreover, it will be further appreciated in reference to FIG. 4 that the lens 82 is disposed within device 10 such that the rear focal point 86 of lens 82 is substantially coincident with a portion of surface 66 of scanning mirror 62 which lies on axis 74. It will now also be understood that scanner 72 oscillates scanning mirror 62 through an arc which is appropriately sized for the focal length 88 and width 90 of lens 82.

As disclosed above, the scanned beam 60 which is reflected from scanning mirror 62 along lines 80 is continuously changing its orientation relative to lens 82. Accordingly, the function of lens 82 is to refract beam 60 from the non-parallel orientations at which it is incident on lens 82 so that scanned beam 60 exits lens 82 along substantially co-parallel lines 96. It is therefore to be appreciated that the particular material, dimensions, and shape of lens 82, which establishes light refraction characteristics of lens 82, will vary according to the particular wavelength of the laser beam produced by source 56. For most wavelengths of scanned beam 60, lens 82 has a width 90 which is approximately one and one-half (1.5) inches long. Additionally, lens 82 has a depth 92 approximately one-quarter (0.25) inches long, and a breadth 94 approximately one-half (0.5) inch long. As was the case for reflecting surfaces 66, 68 of mirrors 62, 64, respectively, lens 82 is thinly coated with an anti-reflection coating to minimize energy loss from scanned beam 60.

Still referring to FIGS. 2 and 4, it may be seen that scanned beam 60 emerges from lens 82 in substantially co-parallel paths as indicated by lines 96. It will be appreciated by the skilled artisan that by so aligning the previously divergent paths of scanned beam 60, lens 82 facilitates maximum transmission of laser light energy into and through focussing blade 14. As seen in FIG. 4, the focussing blade 14 is a relatively flat focussing lens which directs the laser energy that is incident on line 100 of face 102 onto focusing line 44, shown in FIG. 2.

As shown in FIG. 4, the breadth 104 of focussing blade 14 is approximately one and one-quarter (1.25) inches long. Moreover, in order to focus the laser beam 60 as it is directed along co-parallel scanned lines 96, faces 102, 106 of blade 14 are convex. In addition, while focussing blade 14 may be made of any material suitable for focussing beam 60, focussing blade 14 is preferably sapphire. It will be understood that as was the case with lens 82, selection of the particular material of focussing blade 14 will depend in part on the wavelength of the laser beam which is generated by source 56. Moreover, focussing blade 14 may be coated on selected portions of its exterior surface (i.e. surfaces 108 and 110) with a high durability anti-reflection coating, to enhance the light transmission characteristics through blade 14.

OPERATION

In the operation of thermally assisted shaving device 10, reference is initially made to FIGS. 1, 2 and 3. After electrical connections are made with appropriate power supplies, device 10 may be energized by depressing switch 18 to complete the electrical circuits in device 10. For the embodiment shown in FIG. 3, heating element 15 is thereby energized with electricity and accordingly dissipates the electrical energy as heat. Device 10 may then be positioned against the surface to be shaved and moved across the surface in the direction of arrow 38. Consequently, hair which is adjacent heating edge 32 of heating element 15 is heated and softened for easier cutting by blade 46. More specifically, heating element 15 pre-heats and thereby softens hair along heating edge 32 prior to the hair being cut by blade 46. This makes the hair easier to cut, which in turn permits the use of a relatively less sharp blade 46.

In the operation of the embodiment of device 10 shown in FIGS. 2 and 4, it can be seen that upon energizing device 10, the laser source 56 generates the laser beam 54, which is transformed into the collimated beam 60 by collimator 58. Upon emerging from collimator 58, beam 60 is reflected by folding mirror 64 onto scanning mirror 62. In accordance with previous disclosure, scanning mirror 62 is oscillated at an oscillation frequency in the range 100-200 Hz by galvanometric scanner 72 to scan beam 60 along the lines 80 onto lens 82. The now-scanned beam 60 is refracted by scan lens 82 into co-parallel paths 96, and is thus directed by lens 82 onto incident edge 102 of focussing blade 14.

Beam 60 is subsequently focussed into line 44 as it passes through blade 14. More specifically, as beam 60 emerges from blade 14, it is focussed along the line 44 to a diameter of a few microns. Thus, when device 10 is positioned adjacent the surface to be shaved, beam 60 preheats and thereby softens hair along line 44 for easier cutting of the hair by blade 12. This makes the hair easier to cut, which in turn permits the use of a relatively less sharp blade 12.

While the particular thermally assisted shaving device as herein shown and disclosed in detail is fully capable of obtaining the objects and providing the advantages herein before stated, it is to be understood that it is merely illustrative of the presently preferred embodiments of the invention and that no limitations are intended to the details of construction or design herein shown other than as defined in the appended claims.

I claim:

1. A device for shaving hair, which comprises:
   a housing;
   a blade mounted on said housing, said blade having a linear cutting edge projecting from said housing for cutting said hair; and
   a heating means mounted on said housing, said heating means having an elongated edge projecting from said housing and disposed substantially parallel to said blade cutting edge for heating said hair prior to cutting of said hair by said cutting edge.

2. A device for shaving hair as recited in claim 1 wherein said heating means comprises a heating element having a thermal resistance and a source of electricity connected to said element to heat said element.

3. A device for shaving hair as recited in claim 2 wherein said source of electricity is mounted in said housing.

4. A device for shaving hair as recited in claim 2 wherein said heating element is formed with a bevelled heating edge, said edge being bevelled to increase heat dissipation from said edge.

5. A device for shaving hair as recited in claim 1 wherein said heating means comprises a laser for generating a laser beam.

6. A device for shaving hair as recited in claim 5 wherein said laser linearly scans said beam across said surface.

7. A device for cutting hair, which comprises:
   means for cutting said hair, said cutting means having a linear cutting edge;
   means for heating said hair substantially at said cutting edge, said heating means having an elongated edge disposed substantially parallel to said blade cutting edge; and
   means for holding said cutting means and said heating means.

8. A device for cutting hair as recited in claim 7 wherein said cutting means is a razor blade.

9. A device for cutting hair as recited in claim 7 wherein said holding means comprises a housing for holding said cutting means and said heating means.

10. A device for cutting hair as recited in claim 7 wherein said heating means comprises a heating element having a thermal resistance and a source of electricity connected to said element to heat said element.

11. A device for cutting hair as recited in claim 10 wherein said source of electricity is mounted in said housing.

12. A device for cutting hair as recited in claim 10 wherein said heating element is formed with a bevelled heating edge, said edge being bevelled to increase heat dissipation from said edge.

13. A device for cutting hair as recited in claim 7 wherein said heating means comprises a laser for generating a laser beam.

14. A device for cutting hair as recited in claim 13 wherein said laser linearly scans said beam across said surface.

15. A method for cutting hair, comprising the steps of:
   mounting a blade having a substantially straight cutting edge on a housing, said cutting edge extending outwardly from said housing;
   providing heat along a defined line substantially parallel to said cutting edge for heating said hair substantially at said cutting edge prior to cutting said hair with said blade; and
   cutting said hair.

16. A method for cutting hair as recited in claim 15 wherein said heating step is accomplished by directing a laser beam onto the surface to be shaved.

17. A method for cutting hair as recited in claim 15 wherein said heating step is accomplished by positioning a heating element adjacent said hair and heating said element.

* * * * *